United States Patent [19]

Nedelec et al.

[11] 4,177,292
[45] Dec. 4, 1979

[54] NOVEL 5H-BENZOCYCLOHEPTEN-7-AMINES

[75] Inventors: Lucien Nedelec, Le Raincy; Daniel Frechet, Paris; Claude Dumont, Nogent-sur-Marne; Peter Hunt, Gonesse, all of France

[73] Assignee: Roussel Uclaf, Paris, France

[21] Appl. No.: 959,943

[22] Filed: Nov. 13, 1978

[30] Foreign Application Priority Data

Nov. 18, 1977 [FR] France ................... 77 34738

[51] Int. Cl.² .................. A61K 31/135; C07C 91/16; C07C 91/28; C07C 91/40
[52] U.S. Cl. ..................................... 424/330; 260/571
[58] Field of Search ............... 424/330; 260/570.5 R, 260/507.5 CA, 571

[56] References Cited

U.S. PATENT DOCUMENTS

| 3,651,143 | 3/1922 | Galantay | 424/330 |
|-----------|--------|----------|---------|
| 4,091,115 | 5/1978 | Nedelec et al. | 424/330 |

FOREIGN PATENT DOCUMENTS 22734 3/1978 France ................... 424/330

OTHER PUBLICATIONS

Chem. Abst. 68 87060(v) (1968)—Khanna et al.

Primary Examiner—Douglas W. Robinson
Attorney, Agent, or Firm—Hammond & Littell

[57] ABSTRACT

Novel 5H-benzocyclohepten-7-amines of the formula.

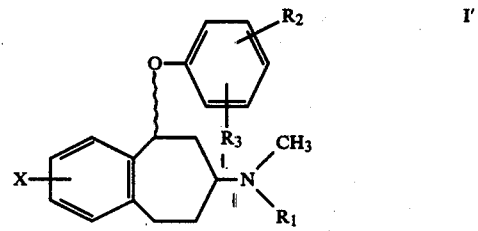

wherein $R_1$ is selected from the group consisting of hydrogen and methyl, $R_2$ and $R_3$ are individually selected from the group consisting of hydrogen, fluorine, chlorine, bromine, nitro, amino, —$CF_3$ and methoxy, X is selected from the group consisting of hydrogen and halogen, and their non-toxic, pharmaceutically acceptable acid addition salts having remarkable in vivo and in vitro inhibiting properties for the capture of serotonine and their preparation.

26 Claims, No Drawings

NOVEL 5H-BENZOCYCLOHEPTEN-7-AMINES

STATE OF THE ART

Commonly assigned U.S. Pat. No. 4,091,115 and copending, commonly assigned U.S. patent application Ser. No. 713,817 filed Aug. 12, 1976 disclose benzocyclohepten-7-amino compounds.

OBJECTS OF THE INVENTION

It is an object of the invention to provide novel 5H-benzocycloheptene-7-amines of formula I' and their non-toxic, pharmaceutically acceptable acid addition salts and to a process for their preparation.

It is another object of the invention to provide novel compositions and a novel method for inhibiting the capture of serotonine in warm-blooded animals.

These and other objects and advantages of the invention will become obvious from the following detailed description.

THE INVENTION

The novel 5H-benzocycloheptene-7-amines of the invention are selected from the group consisting of compounds of the formula

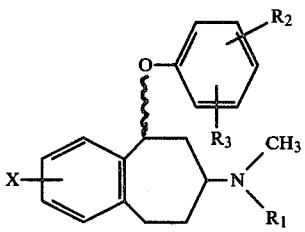

wherein R₁ is selected from the group consisting of hydrogen and methyl, R₂ and R₃ are individually selected from the group consisting of hydrogen, fluorine, chlorine, bromine, nitro, amino, —CF₃ and methoxy, X is selected from the group consisting of hydrogen and halogen, and their non-toxic, pharmaceutically acceptable acid addition salts. The preferred compounds are those wherein X is hydrogen. The wavy line indicates that the substituent in the 5 position may be in the cis or trans form.

Examples of suitable acids for the formation of the acid addition salts are mineral acids such as hydrochloric acid, hydrobromic acid, hydroiodic acid, nitric acid, sulfuric acid, phosphoric acid, etc. and organic acids such as formic acid, acetic acid, benzoic acid, maleic acid, fumaric acid, succinic acid, tartaric acid, citric acid, oxalic acid, glyoxylic acid, aspartic acid, alkanesulfonic acids such as methanesulfonic acid or ethanesulfonic acid, arylsulfonic acids such as benzene sulfonic acid or toleune sulfonic acid.

Among the preferred compounds of the invention are compounds of the formula

I especially those wherein R₁ is methyl and wherein R₂ and R₃ have the above values and preferably at least one of R₂ and R₃ is hydrogen and their non-toxic, pharmaceutically acceptable acid addition salts. Specific preferred compounds are cis and trans isomers of N,N-dimethyl-5-[4-nitrophenyloxy]-6,7,8,9-tetrahydro-5H-benzocycloheptene-7-amine, cis isomer of N,N-dimethyl-6,7,8,9-tetrahydro-5-[4-trifluoromethylphenyloxy]-5H-benzocycloheptene-7-amine and the cis isomer of N,N-dimethyl-6,7,8,9-tetrahydro-5-[4-bromophenyloxy]-5H-benzocycloheptene-7-amine and their non-toxic, pharmaceutically acceptable acid addition salts.

The novel process of the invention for the preparation of a compound of formula I' comprises reacting a compound of the formula

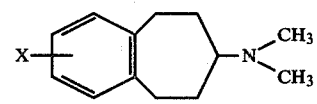

wherein X has the above definition with a compound of the formula

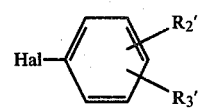

wherein Hal is fluorine, chlorine or bromine, R₂' is selected from the group consisting of fluorine, chlorine, bromine, nitro, —CF₃ and methoxy and R₃' is selected from the group consisting of hydrogen and R₂' to obtain a compound of the formula

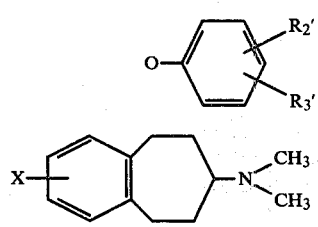

and wherein R₂' or R₃' is nitro, the compound of formula I_A may be reduced to obtain a compound of the formula

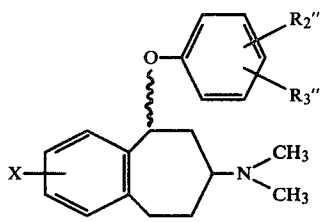

wherein at least one of $R_2''$ and $R_3''$ is amino and the other has the significance of $R_2'$, and when $R_2'$ is bromine and $R_3'$ is hydrogen, the compound of formula $I_A$ may be subjected to hydrogenolysis to obtain an compound of the formula

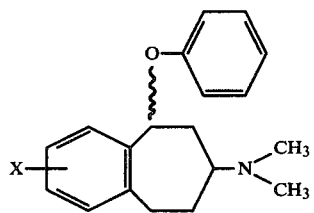

and the products of formulae $I_A$, $I_B$ and $I_C$ may be salified if desired and any of the latter may be desalkylated to form the corresponding compound of formula $I'$ wherein $R_1$ is hydrogen.

The isomeric form of the products is not effected by the process of the invention and when the starting compound of formula II is cis, the compound of formula I′ will be cis and the same is true for the trans isomer.

Among the preferred conditions of the process of the invention, the reaction of the compounds of formulae II and III is effected in the presence of sodium hydride in tetrahydrofuran or more preferably in dimethysulfoxide. The reduction of a compound of formula $I_A$ to form a compound of formula $I_B$ is effected with hydrogen in the presence of a catalyst such as platinum dioxide in a lower alkanol such as ethanol and the hydrogenolysis of a compound of formula $I_A$ to form a compound of formula $I_C$ is effected with hydrogen in the presence of a catalyst such as palladium in a lower alkanol such as ethanol. The desalkylation of a compound of formual I′ is effected with an intermediate of an alkyl haloformate such as ethyl chloroformate in an organic solvent such as benzene or with ethyl azodicarboxylate and is followed by acid or alkaline hydrolysis.

Since the compounds of formula I′ are basic in nature, the compounds may be reacted with a substantially stoichiometric amount of an organic or inorganic acid to form the corresponding acid addition salt.

The novel compositions for the inhibition of serotonine capture are comprised of an effective amount of at least one compound of formula I′ or a non-toxic, pharmaceutically acceptable acid addition salt and an inert pharmaceutical carrier or excipient. The compositions may be in the form of tablets, dragees, gelules, granules, suppositories and injectable solutions or suspensions.

Examples of suitable excipients for the compositions are talc, arabic gum, lactose, starch, magnesium stearate, cacao butter, aqueous or non-aqueous vehicles, fats of animal or vegetable origin, paraffinic derivatives, glycols, diverse wetting agents, emulsifiers and dispersants and preservatives. Especially preferred are cis and trans isomers of N,N-dimethyl-5-[4-nitrophenyloxy]-6,7,8,9-tetrahydro-5H-benzocycloheptene-7-amine, cis isomer of N,N-dimethyl-6,7,8,9-tetrahydro-5-[4-trifluoromethylphenyloxy]-5H-benzocycloheptene-7-amine and the cis isomer of N,N-dimethyl-6,7,8,9-tetrahydro-5-[4-bromophenyloxy]-5H-benzocycloheptene-7-amine and their non-toxic, pharmaceutically acceptable acid addition salts.

The compositions are useful for the treatment of depressions, melancholy, manic-depressive psychosis, reaction from exhaustion depressions and neurotic depressions. Some of the compounds of formula I′ and especially the fumarate of N,N-dimethyl-5-[4-nitrophenyloxy]-6,7,8,9-tetrahydro-5H-benzocycloheptene-7-amine also possess anorexigenic properties and are useful for treating obesity.

The novel method of the invention for treating depressions in warm-blooded animals, including humans, comprises administering to warm-blooded animals an effective amount of at least one compound of formula I′ or its non-toxic, pharmaceutically acceptable acid addition salts. The compounds may be administered orally, rectally or parenterally. The usual daily dose is 0.1 to 6 mg/kg depending on the compound and the method of administration.

The starting compounds of formula II may be prepared by the process of French Pat. No. 2,319,332. The cis and trans isomers of 7-dimethylamino-6,7,8,9-tetrahydro-5H-benzocycloheptene-5-ol may be separated from mixtures thereof by crystallization or chromatography over silica gel.

In the following examples there are described several preferred embodiments to illustrate the invention. However, it should be understood that the invention is not intended to be limited to the specific embodiments.

EXAMPLE 1 fumarate of cis
N,N-dimethyl-5-[4-nitrophenyloxy]-6,7,8,9-tetrahydro-5H-benzocycloheptene-7-amine STEP A: cis and trans
7-dimethylamino-6,7,8,9-tetrahydro-5H-benzocycloheptene-5-ol 27.2 g of a mixture of cis and trans isomers of 7-dimethylamino-6,7,8,9-tetrahydro-5H-benzocycloheptene-5-ol [produced by the process of French patent No. 2,319,332] by chromatography over silica gel and elution with an 8-2 ethyl acetate-triethylamine mixture yielded after removal of the solvent 8.8 g of a first fraction with an Rf=0.2 (trans isomer) and 14.5 g of a second fraction with an Rf=0.10 (cis isomer).

The 14.5 g of the second fraction were dissolved in a minimum of isopropyl ether and the mixture was vacuum filtered to obtain 12 g of the cis isomer. For analysis, the product was crystallized from ether to obtain the cis isomer in the form of colorless crystals melting at 140° C.

Analysis: $C_{13}H_{19}NO$; molecular weight=205.28; Calculated: %C 76.05, %H 9.33, %N 6.82; Found: %C 76.1, %H 9.6, %N 6.8.

The 8.8 g of the first fraction were taken up in a minimum of isopropyl ether and the mixture was vacuum filtered to obtain 8.1 g of the trans product. For analysis, the product was crystallized from ether to obtain the trans isomer in the form of colorless crystals melting at 125° C.

Analysis: $C_{13}H_{19}NO$; molecular weight=205.28; Calculated: %C 76.05, %H 9.33, %N 6.82; Found: %C 75.9, %H 9.6, %N 6.8.

STEP B: fumarate of cis N,N-dimethylamino-5-[4-nitrophenoxy]-6,7,8,9-tetrahydro-5H-benzocycloheptene-7-amine 10 ml of dimethylsulfoxide were added at room temperature to a 50% dispersion of 960 mg of sodium hydride in oil and the mixture was stirred for 20 minutes at 40°-45° C. The mixture was cooled to 25° C. and 4.1 g of the cis isomer of Step A were added thereto. The mixture was stirred for 10 minutes at 25° C. and after the addition of 3.15 g of p-chloronitrobenzene, the mixture was stirred for another 20 minutes at room temperature. The mixture was extracted with methylene chloride and the organic phase was washed with water, dried over magnesium sulfate, filtered and evaporated to dryness under reduced pressure to obtain 8.7 g of raw product. The latter was extracted 3 times with 100 ml of 0.5 N hydrochloric acid and the neutral fraction was washed 3 times with 100 ml of ether. The combined aqueous phases were made alkaline with 50 ml of concentrated ammonium hydroxide and were extracted with methylene chloride. The organic phase was dried over magnesium sulfate, filtered and evaporated to dryness under reduced pressure to obtain 7 g of the cis form of N,N-dimethyl-5-[4-nitrophenoxy]-6,7,8,9-tetrahydro-5H-benzocycloheptene-7-amine in the form of a brown oil.

2.32 g of fumaric acid were partially dissolved in 25 ml of methanol and a solution of 7 g of the cis isomer in 50 ml of isopropanol were added to the suspension. The mixture was heated until dissolution and was then concentrated under a slight vacuum. The mixture stood for 2 hours at room temperature and was then vacuum filtered to obtain 7.4 g of the fumarate of cis N,N-dimethyl-5-[4-nitrophenoxy]-6,7,8,9-tetrahydro-5H-benzocycloheptene-7-amine in the form of colorless crystals melting at 194° C.

Analysis: $C_{19}H_{22}N_2O_3.C_4H_4O_4$; molecular weight=442.45; Calculated: %C 62.43, %H 5.92, %N 6.33; Found: %C 62.2, %H 6.1, %N 6.1.

EXAMPLE 2 cis N,N-dimethyl-5-[4-aminophenoxy]-6,7,8,9-tetrahydro-5H-benzocycloheptene-7-amine dihydrochloride 370 mg of platinum dioxide were added to a solution of 3.7 g of cis N,N-dimethyl-5-[4-nitrophenoxy]-6,7,8,9-tetrahydro-benzocycloheptene-7-amine in 200 ml of ethanol and one liter of hydrogen was bubbled therethrough for 30 minutes with stirring. The mixture was filtered and the filtrate was evaporated to dryness under reduced pressure to obtain 3.6 g of cis N,N-dimethyl-5-[4-aminophenoxy]-6,7,8,9-tetrahydro-5H-benzocycloheptene-7-amine in the form of an orange oil. The said oil was dissolved in 20 ml of ethyl acetate and a solution of ethyl acetate saturated with gaseous hydrogen chloride was added thereto to adjust the pH to 1. The mixture stood for one hour at room temperature and was then vacuum filtered to obtain 4.1 g of the dihydrochloride of the cis compound in the form of colorless crystals melting at $\approx 260°$ C.

Analysis: $C_{19}H_{24}N_2O.2HCl$; molecular weight=369.33; Calculated: %C 61.78, %H 7.10, %N 7.59, %Cl 19.20; Found: %C 61.5, %H 7.1, %N 7.6, %Cl 19.2.

EXAMPLE 3 cis N,N-dimethyl-5-[4-trifluoromethylphenoxy]-6,7,8,9-tetrahydro-5H-benzocycloheptene-7-amine hydrochloride 20 ml of anhydrous dimethylsulfoxide were added at room temperature to 2 g of sodium hydride as a 50% dispersion in oil and the mixture was stirred at 50° C. for 30 minutes and was then cooled to 25° C. 6 g of cis 7-dimethylamino-6,7,8,9-tetrahydro-5H-benzocyclohepten-5-ol were added thereto and the mixture was stirred for 15 minutes after which 5.35 ml of p-bromo-trifluoromethylbenzene were added thereto. The mixture was heated at 50° C. for 4 hours and was cooled to 20°-25° C. 200 ml of water were added thereto and the mixture was extracted with methylene chloride. The organic phase was washed with water, dried and evaporated to dryness to obtain 12.35 g of raw product. The latter was chromatographed over silica gel and elution with a 7-3 chloroform-methanol mixture yielded after evaporation of the solvent 7.3 g of cis N,N-dimethyl-5-[4-trifluoromethylphenoxy]-6,7,8,9-tetrahydro-5H-benzocycloheptene-7-amine in the form of an orange oil. The said product was dissolved in 30 ml of ethyl acetate and an excess of a solution of gaseous hydrogen chloride in ethyl acetate was added thereto. Crystallization occured and the mixture was vacuum filtered. The recovered precipitate was washed with ethyl acetate and was dried to 60° C. under reduced pressure to obtain 7.2 g of the hydrochloride of the cis compound melting at $\approx 230°$ C.

Analysis: $C_{20}H_{22}F_3NO.HCl$; molecular weight=385.86; Calculated: %C 62.26 %H 6.01 %Cl 9.19 %F 14.77 %N 3.63; Found: %C 62.4 %H 5.9 %Cl 9.2 %F 14.5 %N 3.4.

EXAMPLE 4 trans N,N-dimethyl-5-[4-nitrophenoxy]-6,7,8,9-tetrahydro-5H-benzocycloheptene-7-amine hydrochloride 14.4 ml of anhydrous dimethylsulfoxide were added at room temperature to 1.44 g of sodium hydride as a 50% dispersion in oil and the mixture was heated in a bath at 55° C. for one hour and was then cooled to 20° C. 5.13 g of trans 7-dimethylamino-6,7,8,9-tetrahydro-5H-benzocycloheptene-5-ol were added thereto and the mixture was stirred at room temperature for 10 minutes. Then, 4.73 g of p-chloro-nitrobenzene were added thereto all at once and the mixture was stirred at room temperature for 3 hours. The mixture was extracted with methylene chloride and the organic phase was washed with water, dried over magnesium sulfate and evaporated to dryness under reduced pressure to obtain 9.5 g of raw product. The latter was extracted with 0.5 N hydrochloric acid and the neutral fraction was extracted twice with 100 ml of ether. The combined aqueous phases were made alkaline with a strong excess of ammonium hydroxide and were extracted with methylene chloride. The organic phase was dried over magnesium sulfate and filtered and the filtrate was evaporated to dryness under reduced pressure to obtain 8.5 g of trans N,N-dimethyl-5-[4-nitrophenoxy]-6,7,8,9-tetrahydro-5H-benzocycloheptene-7-amine. The said product was dissolved in 20 ml of ethyl acetate and an excess of a solution of gaseous hydrogen chloride in ethyl acetate was added thereto. Crystallization was induced and the mixture was held in the refrigerator for 12 hours and was then vacuum filtered. The recovered precipitate was washed with methyl ethyl ketone and was dried at 100° C. under reduced pressure to obtain 5.5 g of the hydrochloride of the trans compound in the form of colorless crystals melting at 192°–196° C.

Analysis: $C_{19}H_{22}N_2O_3.HCl$; molecular weight=362.85; Calculated: %C 62.89, %H 6.39, %N 7.72, %Cl 9.77; Found: %C 63.0, %H 6.5, %N 7.8, %Cl 10.1.

EXAMPLE 5 cis N,N-dimethyl-5-[2-trifluoromethylphenoxy]-6,7,8,9-tetrahydro-5H-benzocycloheptene-7-amine hydrochloride A mixture of 14 ml of dimethylsulfoxide and 1.4 g of sodium hydride as a 50% oil dispersion was heated to 50° C. for 50 minutes and after cooling to 20° C., 4 g of cis 7-dimethylamino-6,7,8,9-tetrahydro-5H-benzocyclohepten-5-ol were added thereto. The mixture was held at 20° C. for 15 minutes and then 3.2 ml of o-bromo-trifluoromethylbenzene were added thereto. The mixture was heated to 100°±5° C. for 2¾ hours and was added to 20° C. and extracted with methylene chloride. The organic phase was washed with water, dried and evaporated to dryness under reduced pressure to obtain 7.8 g of raw product. The latter was chromatographed over silica gel and was eluted with methylene chloride containing 5% of methanol. The solvent was evaporated to obtain 5.5 g of cis N,N-dimethylamino-5-[2-trifluoromethylphenoxy]-6,7,8,9-tetrahydro-5H-benzocycloheptene-7-amine in the form of an oil.

The oil was dissolved in 30 ml of ethyl acetate and the solution was acidified with an excess of a solution of gaseous hydrogen chloride in ethyl acetate. The mixture was vacuum filtered and the recovered precipitate was washed with ethyl acetate and was dried under reduced pressure to obtain 4.6 g of the hydrochloride of the cis compound in the form of colorless crystals melting at $\approx$220° C.

Analysis: $C_{20}H_{22}F_3NO.HCl$; molecular weight=385.86; Calculated: %C 62.26, %H 6.01, %Cl 9.19, %N 3.63, %F 14.77; Found: %C 62.1, %H 6.1, %Cl 9.4, %N 3.5, %F 14.5.

EXAMPLE 6 cis N-methyl-5-[4-trifluoromethylphenoxy]-6,7,8,9-tetrahydro-5H-benzocycloheptene-7-amine hydrochloride

STEP A: cis ethyl N-methyl-N-[6,7,8,9-tetrahydro-5-(4-trifluoromethylphenoxy)-5H-benzocyclohepten-7-yl]-carbamate 7.4 g of the hydrochloride of cis N,N-dimethyl-5-[4-trifluoromethylphenoxy]-6,7,8,9-tetrahydro-5H-benzocycloheptene-7-amine were empasted with 70 ml of water and the mixture was made alkaline by addition of concentrated ammonium hydroxide. The mixture was extracted with methylene chloride and the organic phase was washed with water, dried and evaporated to dryness to obtain 6.85 g of the free cis base. The latter was dissolved in 60 ml of benzene and 60 ml of ethyl chloroformate were added thereto under nitrogen. The mixture was refluxed for 16 hours and was evaporated to dryness. The residue was taken up in ether and the ether phase was washed with N hydrochloric acid and then with water, dried over magnesium sulfate, treated with activated carbon and was filtered. The filtrate was evaporated to dryness to obtain 8.17 g of raw product which was chromatographed over silica gel. Elution with methylene chloride and evaporation of the eluant yielded 7.1 g of cis ethyl N-methyl-N-[6,7,8,9-tetrahydro-5-(4-trifluoromethylphenoxy)-5H-benzocyclohepten-7-yl]-carbamate in the form of a colorless oil.

STEP B: cis N-methyl-5-[4-trifluoromethylphenoxy]-6,7,8,9-tetrahydro-5H-benzocyclohepten-7-amine hydrochloride A solution of 7.1 g of the product of Step A in 70 ml of n-butanol was mixed with stirring under nitrogen with 7 g of potassium hydroxide pastilles and the mixture was then refluxed for 17 hours. The mixture was evaporated to dryness and the residue was taken up in methylene chloride. The solution was washed with water and dried and evaporated to dryness to obtain 5.5 g of cis N-methyl-5-[4-trifluoromethylphenoxy]-6,7,8,9-tetrahydro-5H-benzocyclohepten-7-amine in the form of an orange oil. The latter was dissolved in 30 ml of ethyl acetate and the solution was made acidic by addition of a solution of gaseous hydrogen chloride in ethyl acetate. Crystallized was effected and the mixture was vacuum filtered. The recovered product was washed with ethyl acetate and was dried to obtain 5.4 g of the hydrochloride of the cis product in the form of white crystals melting at $\approx$220° C.

Analysis: $C_{19}H_{20}F_3NO.HCl$; molecular weight=371.84; Calculated: %C 61.37, %H 5.69, %N 3.77, %Cl 9.53, %F 15.33; Found: %C 61.3, %H 5.8, %N 3.6, %Cl 9.5, %F 15.2.

EXAMPLE 7 cis N,N-dimethyl-5-[4-bromophenoxy]-6,7,8,9-tetrahydro-5H-benzocyclohepten-7-amine hydrochloride A mixture of 8 ml of dimethylsulfoxide and 0.820 g of sodium hydride as a 50% oil dispersion was heated at 50° C. for 45 minutes and was then cooled to 20° C. 3 g of cis 7-dimethylamino-6,7,8,9-tetrahydro-5H-benzocyclohepten-5-ol were added thereto and the mixture stood at room temperature for 15 minutes after which 2 ml of p-bromo-fluorobenzene were added thereto. The mixture was heated at 90°±5° C. for one hour and was then cooled to 20° C. and extracted with methylene chloride. The organic phase was washed with water, dried and evaporated to dryness to obtain 6 g of cis N,N-dimethyl-5-[4-bromophenoxy]-6,7,8,9-tetrahydro-5H-benzocyclohepten-7-amine in the form of a yellow oil.

The oil was dissolved in 30 ml of ethyl acetate and the solution was made acidic by addition of a solution of gaseous hydrogen chloride in ethyl acetate. Crystallization was effected at 20° C. for one hour and the mixture was vacuum filtered. The recovered precipitate was washed with ethyl acetate and was dried to obtain 4.8 g of the hydrochloride of the cis compound in the form of colorless crystals melting at about 230° C.

Analysis: $C_{19}H_{22}BrNO.HCl$; molecular weight=396.76; Calculated: %C 57.52, %H 5.84, %N 3.53, %Br 20.14, %Cl 8.94; Found: %C 57.2, %H 6.0, %N 3.6, %Br 19.7, %Cl 8.8.

EXAMPLE 8 cis N,N-dimethyl-5-[2-nitrophenoxy]-6,7,8,9-tetrahydro-5H-benzocyclohepten-7-amine hydrochloride A mixture of 11 ml of dimethylsulfoxide and 1.1 g of hydroxide as a 50% oil dispersion was heated in a bath at 70° C. for 30 minutes and after cooling the mixture to 20° C., 4.1 g of cis 7-dimethylamino-6,7,8,9-tetrahydro-5H-benzocyclohepten-5-ol were added thereto. The mixture was stirred for 10 minutes at room temperature and then 6.32 g of o-chloronitrobenzene were added thereto while cooling in an ice bath. The mixture was stirred for 30 minutes at 20° C. and was extracted with methylene chloride. The organic phase was washed with water, dried over magnesium sulfate and was filtered. The filtrate was evaporated to dryness under reduced pressure to obtain 12.8 g of cis N,N-dimethyl-5-[2-nitrophenoxy]-6,7,8,9-tetrahydro-5H-benzocyclohepten-7-amine in the form of a brown oil.

The said oil was taken up in 30 ml of water and 2 ml of 2 N hydrochloric acid were added thereto. The mixture was vacuum filtered and the recovered product was washed with water, then with ether and dried at 65° C. under reduced pressure to obtain 5.9 g of the hydrochloride of the cis compound which after crystallization from refluxing ethanol was in the form of yellow flakes melting at ≈240° C.

Analysis: $C_{19}H_{22}N_2O_3$. HCl; molecular weight=362.84; Calculated: %C 62.89, %H 6.39, %Cl 9.77, %N 7.72; Found: %C 62.8, %H 6.5, %Cl 9.8, %N 7.6.

EXAMPLE 9 cis N-methyl-5-[4-nitrophenoxy]-6,7,8,9-tetrahydro-5H-benzocyclohepten-7-amine hydrochloride 348 mg of diethyl azocarboxylate were added to a mixture of 652 mg of cis N,N-dimethyl-5-[4-nitrophenoxy]-6,7,8,9-tetrahydro-5H-benzocyclohepten-7-amine in 10 ml of acetone and the mixture was refluxed for 3½ hours. The acetone was distilled under reduced pressure and 5 ml of N hydrochloric acid were added to the residue. The mixture was stirred at room temperature for 26 hours and was then made alkaline with ammonium hydroxide. The mixture was extracted with methylene chloride and the organic phase was washed with water, dried over magnesium sulfate and filtered. The filtrate was evaporated to dryness under reduced pressure to obtain 1.1 g of raw product which was chromatographed over silica gel. Elution with a 7-3 chloroform-methanol mixture yielded 400 mg of cis N-methyl-5-[4-nitrophenoxy]-6,7,8,9-tetrahydro-5H-benzocyclohepten-7-amine. The said product was dissolved in ethyl acetate containing gaseous hydrogen chloride and 380 mg of the hydrochloride of the cis compound melting at 265° C. was recovered therefrom.

Analysis: $C_{18}H_{20}N_2O_3$.HCl; molecular weight=348.83; Calculated: %C 61.97, %H 6.07, %Cl 10.16, %N 8.03; Found: %C 61.9, %H 6.2, %Cl 10.2, %N 7.8.

EXAMPLE 10 cis N,N-dimethyl-5-[2-methoxyphenoxy]-6,7,8,9-tetrahydro-5H-benzocyclohepten-7-amine hydrochloride 14 ml of dimethylsulfoxide were added dropwise to 1.4 g of sodium hydride as a 50% oil dispersion and the mixture was heated at 60° C. for 25 minutes and was then cooled to 25° C. 5 g of cis 7-dimethylamino-6,7,8,9-tetrahydro-5H-benzocyclohepten-5-ol were added thereto and after the mixture stood at room temperature for 15 minutes, 10.7 ml of o-fluoroanisole were added thereto. The mixture was heated at 90°±5° C. for 4½ hours and was then cooled to 25° C. and was extracted with methylene chloride. The organic phase was washed with water, dried and evaporated to dryness at 60° C. under reduced pressure to obtain 8.5 g of raw product. The latter was chromatographed over silica gel and was eluted with a 7-3 chloroform-methanol mixture to obtain after evaporation of the solvent, 5.4 g of cis N,N-dimethyl-5-[2-methoxyphenoxy]-6,7,8,9-tetrahydro-5H-benzocyclohepten-7-amine in the form of an orange oil.

The said oil was dissolved in 30 ml of ethyl acetate and the solution was acidified with a solution of gaseous hydrogen chloride in ethyl acetate. The mixture was concentrated and vacuum filtered and the recovered product was washed with ethyl acetate and dried under reduced pressure at 60° C. The product was crystallized from ethanol to obtain 4.45 g of the hydrochloride of the cis compound in the form of colorless crystals melting at 212° C. and then 222° C.

Analysis: $C_{20}H_{25}NO_2$.HCl; molecular weight=347.89; Calculated: %C 69.05, %H 7.53, %N 4.03, %Cl 10.19; Found: %C 68.7, %H 7.5, %N 3.8, %Cl 10.1.

EXAMPLE 11 cis N,N-dimethyl-5-[4-methoxyphenoxy]-6,7,8,9-tetrahydro-5H-benzocyclohepten-7-amine hydrochloride 12 ml of dimethylsulfoxide were added dropwise to 1.16 g of sodium hydride in the form of a 50% oil dispersion and the mixture was heated at 60° C. for 35 minutes and was then cooled to 25° C. Then, 4.1 g of cis 7-dimethylamino-6,7,8,9-tetrahydro-5H-benzocyclohepten-5-ol were added thereto followed 15 minutes later by the addition of 8.8 ml of p-fluoroanisole. The mixture was heated at 90° C. for 46 hours and was then cooled to 25° C. The mixture was extracted with 150 ml of methylene chloride and the organic phase was washed with water, dried and evaporated to dryness under reduced pressure to obtain 5.7 g of raw product. The latter was chromatographed over silica gel and was eluted with a 7-3 chloroform-methanol mixture to obtain, after evaporation of the solvents, 1.7 g of cis N,N-dimethyl-5-[4-methoxyphenoxy]-6,7,8,9-tetrahydro-5H-benzocyclohepten-7-amine in the form of an orange oil.

The oil was dissolved in 15 ml of ethyl acetate and the solution was acidified with a solution of gaseous hydrogen chloride in ethyl acetate. The mixture was concentrated and was vacuum filtered and the recovered product was washed with ethyl acetate and dried under reduced pressure to obtain, after crystallization from ethanol, 1.60 g of the hydrochloride of the cis compound in the form of colorless crystals melting at 215° C.

Analysis: $C_{20}H_{25}NO_2.HCl$; molecular weight=347.89; Calculated: %C 69.05, %H 7.53, %N 4.03, %Cl 10.19; Found: %C 68.9, %H 7.5, %N 3.9, %Cl 10.1.

EXAMPLE 12 cis
N,N-dimethyl-5-[4-chlorophenoxy]-6,7,8,9-tetrahydro-5H-benzocyclohepten-7-amine hydrochloride 0.6 ml of dimethylsulfoxide were added at room temperature to 60 mg of sodium hydride in a 50% oil dispersion and the mixture was heated to 50° C. for 20 minutes and was then cooled to 20° C. 205 mg of cis 7-dimethylamino-6,7,8,9-tetrahydro-5H-benzocyclohepten-5-ol were added thereto and after stirring the mixture for 15 minutes, 0.13 ml of p-chloro-fluorobenzene was added thereto. The mixture stood for one hour at 20° C. and was heated at 50° C. for 90 minutes and for 3 hours at 100° C. The mixture was cooled to 20° C. and was extracted with 30 ml of methylene chloride. The organic phase was washed with water, dried and evaporated to dryness to obtain 300 mg of raw product which was chromatographed over silica gel. Elution with a 7-3 chloroform-methanol mixture and evaporation of the solvent yielded 250 mg of cis N,N-dimethyl-5-[4-chlorophenoxy]-6,7,8,9-tetrahydro-5H-benzocyclohepten-7-amine in the form of an oil.

The oily product was dissolved in 2 ml of ethyl acetate and the solution was acidified with a solution of gaseous hydrogen chloride in ethyl acetate. The mixture was concentrated and vacuum filtered and the recovered precipitate was washed with ethyl acetate and dried to obtain 240 mg of the hydrochloride of the cis product in the form of colorless crystals melting at 215° C.

Analysis: $C_{19}H_{22}ClNO.HCl$; molecular weight=352.31; Calculated: %C 64.77, %H 6.58, %Cl 20.13, %N 3.98; Found: %C 64.7, %H 6.8, %Cl 19.9, %N 3.9.

EXAMPLE 13 cis N,N-dimethyl-5-[phenoxy]-6,7,8,9-tetrahydro-5H-benzocycloheptan-7-amine hydrochloride 330 mg of cis N,N-dimethyl-5-[4-bromophenoxy]-6,7,8,9-tetrahydro-5H-benzocyclohepten-7-amine hydrochloride were empasted with 15 ml of water and 5 ml of ammonium hydroxide (d=0.90) were added thereto. The mixture was extracted with ethyl acetate and the organic phase was washed with water, dried and evaporated to dryness under reduced pressure to obtain 310 mg of the free base. The latter was dissolved in 9 ml of ethanol and 0.35 ml of triethylamine dried over potassium hydroxide were added thereto followed by the addition of 35 mg of 10% palladized carbon. The mixture was hydrogenated at 20° C. with stirring at normal pressure (30 ml of hydrogen absorbed) and was filtered. The filtrate was evaporated to dryness and the residue was added to sodium hydroxide solution. The mixture was extracted with ethyl acetate and the organic phase was washed with water, dried and evaporated to dryness to obtain 235 mg of cis N,N-dimethyl-5-[phenoxy]-6,7,8,9-tetrahydro-5H-benzocyclohepten-7-amine in the form of a yellow oil. The said oil was dissolved in 3 ml of ethyl acetate and the solution was acidified with a solution of gaseous hydrogen chloride in ethyl acetate. The mixture was concentrated and vacuum filtered and the recovered precipitate was washed with ethyl acetate and dried to obtain 215 mg of the hydrochloride of the cis compound in the form of colorless crystals melting at 225° C.

Analysis: $C_{19}H_{23}NO.HCl$; molecular weight=317.86; Calculated: %C 71.80, %H 7.61, %Cl 11.15, %N 4.41; Found: %C 71.6, %H 7.7, %Cl 11.0, %N 4.3.

EXAMPLE 14 cis-N,N-dimethyl-5-[4-fluorophenoxy]-6,7,8,9-tetrahydro-5H-benzocyclohepten-7-amine hydrochloride A mixture of 0.6 ml of dimethylsulfoxide and 60 mg of sodium hydride in the form of a 50% oil dispersion was heated at 60° C. for 25 minutes and was then cooled to 25° C. after which 205 mg of cis 7-dimethylamino-6,7,8,9-tetrahydro-5H-benzocyclohepten-5-ol were added thereto. After 15 minutes, 0.4 ml of p-difluorobenzene were added thereto and the mixture was heated at 90° C. for 6¾ hours and was then cooled to 20° C. The mixture was extracted with methylene chloride and the organic phase was washed with water, dried and evaporated to dryness to obtain 350 mg of raw product which was dissolved in 10 ml of N hydrochloric acid. The solution was washed with ether and made alkaline with sodium hydroxide solution. The mixture was extracted with methylene chloride and the organic phase was washed with water, dried and evaporated to dryness to obtain 270 mg of cis N,N-dimethyl-5-[4-fluorophenoxy]-6,7,8,9-tetrahydro-5H-benzocyclohepten-7-amine in the form of an oil.

The oil was dissolved in 3 ml of ethylacetate and the solution was acidified with a solution of gaseous hydrogen chloride in ethyl acetate. The mixture was concentrated and vacuum filtered and the recovered product was washed with ethyl acetate and dried to obtain 220 mg of the hydrochloride of the cis compound in the form of colorless crystals melting at 208° C.

Analysis: $C_{19}H_{22}FNO.HCl$; molecular weight=335.85; Calculated: %C 67.95, %H 6.90, %Cl 10.56, %F 5.66, %N 4.17; Found: %C 67.6, %H 7.1, %Cl 10.7, %F 5.3, %N 4.1.

EXAMPLE 15 cis
N,N-dimethyl-5-[2-chlorophenoxy]-6,7,8,9-tetrahydro-5H-benzocyclohepten-7-amine hydrochloride 0.6 ml of dimethylsulfoxide were added to 65 mg of sodium hydride in the form of a 50% oil dispersion and the mixture was held at 25° C. for 30 minutes and was then heated to 60° C. and then cooled to 25° C. 205 mg of cis 7-dimethylamino-6,7,8,9-tetrahydro-5H-benzocyclohepten-5-ol were added thereto and after standing at room temperature for 15 minutes, 0.15 ml of o-chlorofluorobenzene was added thereto. The mixture was heated at 80° C. for 30 minutes and then was cooled to 20° C. and extracted with methylene chloride. The organic phase was washed with water, dried and evaporated to dryness to obtain 370 mg of cis N,N-dimethyl-5-[2-chlorophenoxy]-6,7,8,9-tetrahydro-5H-benzocyclohepten-7-amine in the form of an orange oil.

The said oil was dissolved in 4 ml of ethyl acetate and the solution was acidified with a solution of gaseous hydrogen chloride in ethyl acetate. The mixture was concentrated to dryness, washed with the hydrogenchloride-ethyl acetate solution and was dried to obtain 315 mg of the hydrochloride of the cis compound in the form of colorless crystals melting at ≈240° C.

Analysis: C$_{19}$H$_{22}$ClNO.HCl; molecular weight=352.31; Calculated: %C 64.77, %Y 6.58, %Cl 20.12, %N 3.98; Found: %C 64.8, %Y 6.7, %Cl 20.2, %N 3.9.

EXAMPLE 16 cis N,N-dimethyl-5-[3-nitrophenoxy]-6,7,8,9-tetrahydro-5H-benzocyclohepten-7-amine hydrochloride 14 ml of dimethylsulfoxide were added to 1.4 g of sodium hydride in a 50% oil dispersion and the mixture was held at 25° C. for 35 minutes, was heated to 60° C. and then cooled to 25° C. Then, 5 g of cis 7-dimethylamino-6,7,8,9-tetrahydro-5H-benzocyclohepten-5-ol were added thereto and after the mixture stood at room temperature for 15 minutes, 5.3 ml of m-fluoronitrobenzene were added thereto. The mixture was held at 25° C. for 30 minutes and was then extracted with methylene chloride. The organic phase was washed with aqueous sodium chloride solution, was dried and evaporated to dryness to obtain 10.8 g of cis N,N-dimethyl-5-[3-nitrophenoxy]-6,7,8,9-5H-benzocyclohepten-7-amine in the form of a red gum.

The said gum was dissolved in 17 ml of 2 N hydrochloric acid and ether was added thereto. The mixture was iced and vacuum filtered. The recovered product was washed with water, then ether and dried at 80° C. under reduced pressure to obtain 4 g of the hydrochloride of the cis compound. The latter was dissolved in refluxing methanol and ethyl acetate was added thereto. The mixture was vacuum filtered and the filtrate was concentrated, allowed to stand at 20° C. for 12 hours and was then vacuum filtered. The recovered product was washed with ethyl acetate and dried under reduced pressure to obtain 3.5 g of the said hydrochloride in the form of a beige product melting at 216° C.

Analysis: C$_{19}$H$_{22}$N$_2$O$_3$.HCl; molecular weight=262.85; Calculated: %C 62.89, %H 6.39, %Cl 9.77, %N 7.72; Found: %C 62.6, %H 6.3, %Cl 9.9, %N 7.4.

EXAMPLE 17 cis-N,N-dimethyl-5-[4-nitro-3-trifluoromethylphenoxy]-6,7,8,9,-tetrahydro-5H-benzocyclohepten-7-amine 30 ml of anhydrous dimethylsulfoxide were added to 1.5 g of sodium hydride in the form of a 50% oil dispersion and the mixture was stirred at 75° C. for 20 minutes and was then cooled to 20° C. 5.1 g of cis 7-dimethylamino-6,7,8,9-tetrahydro-5H-benzocyclohepten-5-ol were added thereto and the mixture was stirred for 10 minutes and then cooled in an ice bath. 6.7 g of 5-chloro-2-nitro-trifluoromethylbenzene were added thereto and the mixture was stirred at 70° C. for 30 minutes and was then cooled to 20° C. The mixture was extracted with methylene chloride and the organic phase was washed with aqueous sodium chloride solution, dried and evaporated to dryness to obtain 13 g of raw product. The latter was taken up in aqueous hydrochloric acid and the washed with ether, thereafter the solution was made alkaline with ammonium hydroxide. The mixture was extracted with methylene chloride and the organic phase was dried and evaporated to dryness to obtain 9.9 g of a brown oil. The oil was taken up in 200 ml of isopropyl ether at 50° C. and the solution was treated with activated carbon and was filtered. The filtrate was evaporated to dryness under reduced pressure. The residue was treated with 10 ml of isopropyl ether and crystallization was effected. The mixture was vacuum filtered to obtain 5.95 g of product which was crystallized from petroleum ether and then from isopropyl ether to obtain 3.8 g of cis N,N-dimethyl-5-[4-nitro-3-trifluoromethylphenoxy]-6,7,8,9-tetrahydro-5H-benzocyclohepten-7-amine in the form of beige crystals melting at 75° C.

Analysis: C$_{20}$H$_{21}$F$_3$N$_2$O$_3$; molecular weight=394.39; Calculated: %C 60.90, %H 5.37, %F 14.45, %N 7.10; Found: %C 60.6, %H 5.4, %F 14.2, %N 7.1.

EXAMPLE 18 trans N,N-dimethyl-3-chloro-5-[4-nitrophenoxy]-6,7,8,9-tetrahydro-5H-benzocyclohepten-7-amine hydrochloride

STEP A: 3-chloro-7-dimethylamino-6,7,8,9-tetrahydro-5H-benzocyclohepten-5-one A mixture of 9.6 g of 3-chloro-8,9-dihydro-5H-benzocyclohepten-5-one (prepared by process of French Pat. No. 2,319,332) and 15 ml of an ethanolic solution of 33% dimethylamine was stirred at 20° C. for one hour and the mixture was evaporated to dryness to obtain 11.6 g of an orange oil which were dissolved in 60 ml of ethyl acetate. The mixture was acidified by addition of a solution of gaseous hydrogen chloride in ethyl acetate at 5° C. under an inert atmosphere and after standing at 5° C. for 2 hours, the mixture was vacuum filtered. The recovered product was washed with ethyl acetate and was dried to obtain 9.6 g of 3-chloro-7-dimethylamino-6,7,8,9-tetrahydro-5H-benzocyclohepten-5-one in the form of a white solid melting at 146° C. which was used as is for the next step.

STEP B: trans 3-chloro-7-dimethylamino-6,7,8,9-tetrahydro-5H-benzocyclohepten-5-ol A mixture of 1 g of the product of Step A, 1 ml of water, 1 g of sodium borohydride and 10 ml of methanol were stirred at 10° C. under an inert atmosphere for 10 minutes and the mixture was then poured into 50 ml of water. The mixture was extracted with methylene chloride and the organic phase was dried and evaporated to dryness to obtain 900 mg of a yellow oil which was chromatographed over silica gel. Elution with an 8−2 ethyl acetate-triethylamine mixture yielded a 250 mg homogeneous fraction of a yellow oil with an Rf=0.12 which crystallized in ether. The product was crystallized from isopropyl ether to obtain 100 mg of trans 3-chloro-7-dimethylamino-6,7,8,9-tetrahydro-5H-benzocyclohepten-5-ol in the form of colorless crystals melting at 110° C.

Analysis: C$_{19}$H$_{18}$ClNO; molecular weight=239.75; Calculated: %C 65.13, %H 7.57, %N 5.84, %Cl 14.79; Found: %C 65.3, %H 7.6, %N 5.7, %Cl 14.9.

STEP C: trans N,N-dimethyl-3-chloro-5-[4-nitrophenoxy]-6,7,8,9-tetrahydro-5H-benzocyclohepten-7-amine hydrochloride 12 ml of anhydrous dimethylsulfoxide were added under nitrogen to 1.2 g of sodium hydride as a 50% oil dispersion and the mixture was stirred at 60° C. for 30 minutes and was then cooled to 25° C. 4.8 g of trans 3-chloro-7-dimethylamino-6,7,8,9-tetrahydro-5H-benzocyclohepten-5-ol were added thereto and the mixture was stirred for 15 minutes at 25° C. after which 6.3 g of p-chloronitrobenzene were added thereto. The mixture was stirred for one hour and 500 ml of water were added thereto. The mixture was extracted with methylene chloride and the organic phase was dried over magnesium sulfate and was evaporated to dryness under reduced pressure. The residue was taken up in 130 ml of N hydrochloric acid and after standing for 20 minutes, the mixture was vacuum filtered. The recovered product was washed with ether, then water and dried under vacuum to obtain 7.3 g of product which was crystallized from methanol and ethyl acetate to obtain 5 g of trans N,N-dimethyl-3-chloro-5-[4-nitrophenoxy]-6,7,8,9-tetrahydro-5H-benzocyclohepten-7-amino hydrochloride in the form of colorless crystals melting at 230° C.

Analysis: $C_{19}H_{21}ClN_2O_3.HCl$; molecular weight=397.30; Calculated: %C 57.44, %H 5.58, %N 7.05, %Cl 17.85; Found: %C 57.4, %H 5.7, %N 7.1, %Cl 17.8.

EXAMPLE 19 cis N,N-dimethyl-3-chloro-5-[4-nitrophenoxy]-6,7,8,9-tetrahydro-5H-benzocyclohepten-7-amino hydrochloride Using the procedure of Example 18, the 900 mg of oil was chromatographed to obtain 360 mg of a homogeneous fraction of a yellow oil with an Rf=0.06 which was crystallized from ether to obtain 160 mg of cis 3-chloro-7-dimethylamino-6,7,8,9-tetrahydro-5H-benzocyclohepten-5-ol in the form of colorless crystals melting at 140° C. 4.8 g of the said product were reacted as in Example 18 to obtain 5.3 g of cis N,N-dimethyl-3-chloro-5-[4-nitrophenoxy]-6,7,8,9-tetrahydro-5H-benzocyclohepten-7-amine hydrochloride in the form of colorless crystals melting at 255° C.

Analysis: $C_{19}H_{21}ClN_2O_3.HCl$; molecular weight=397.30; Calculated: %C 57.44, %H 5.58, %N 7.05, %Cl 17.85; Found: %C 57.2, %H 5.7, %N 6.9, %Cl 18.0.

EXAMPLE 20

200 mg tablets were prepared with 25 mg of the fumarate of cis N,N-dimethyl-5-[4-nitrophenoxy]-6,7,8,9-tetrahydro-5H-benzocyclohepten-7-amine or the hydrochloride of trans N,N-dimethyl-5-[nitrophenoxy]-6,7,8,9-tetrahydro-5H-benzocycloheptene-7-amine and sufficient excipient of lactose, starch, talc and magnesium stearate.

BIOCHEMICAL STUDY

A. Inhibition of Serotonine uptake in vitro

The inhibition of serotonine (5HT) uptake was measured in impure synaptosomes prepared from the entire brain of a female rat 19 to 21 days old using the technique of Kannengiesser et al [Biochemical Pharmacology, Vol. 22, (1973) p. 73]. Diverse concentrations of the products were placed in an incubator with the preparation at 37° C. for 5 minutes in the presence of 14 C-5HT at a concentration of $10^{-7}$ M. The 50% inhibiting concentration (IC$_{50}$), dose which inhibits by 50% the uptake of 14C-5HT in the synaptosomes was determined graphically and the IC$_{50}$ dose for the compound are reported in Table I.

TABLE I

| Product of Examples | Inhibiting concentration IC$_{50}$ moles |
|---|---|
| 1 | $3.4 \times 10^{-7}$ |

TABLE I-continued

| Product of Examples | Inhibiting concentration IC$_{50}$ moles |
|---|---|
| 2 | $1.4 \times 10^{-5}$ |
| 3 | $7.6 \times 10^{-7}$ |
| 4 | $8.3 \times 10^{-8}$ |
| 5 | $2.3 \times 10^{-6}$ |
| 6 | $1.9 \times 10^{-6}$ |
| 7 | $3.2 \times 10^{-7}$ |
| 8 | $4 \times 10^{-6}$ |
| 10 | $1.3 \times 10^{-6}$ |
| 11 | $1.3 \times 10^{-6}$ |
| 17 | $9.5 \times 10^{-7}$ |
| 18 | $1.5 \times 10^{-6}$ |
| 19 | $7.1 \times 10^{-6}$ |

B. Inhibition of Serotonine uptake in vivo

The tested products were intraperitoneally administered to a groups of female rats 19 to 21 days old at doses of 5 mg/kg. After 1 hour or 24 hours, the brain was removed and synaptosomes were prepared and placed in an incubator in the presence of 14 C-5HT as indicated in the previous test. The relative power of the products to inhibit the uptake of 14C-5HT was estimated with respect to a test effected with animals which did not receive the tested product and the activity was expressed as a percentage of inhibition of the uptake for each time. The results are reported in Table II.

TABLE II

| Product of Examples | % inhibition after | |
|---|---|---|
|  | 1 Hour | 24 Hours |
| 1 | 58 ± 4 | 67 ± 2 |
| 4 | 61 ± 2 | 39 ± 4 |
| 6 | 41 ± 3 | 61 ± 3 |
| 7 | 40 ± 3 | 65 ± 2 |

The results of Tables I and II show that the products possess very interesting serontoinergic properties in the test as established in the time period.

C. Anorexigenic activity

This activity was determined on dogs by the method of Adams et al [J. Pharm. Sci., Vol. 53 (1964), p. 1405] in which the animals received as food exclusively U.A.R. mash with a base of 800 g per day per dog. On the day of the test of a presumed anorexigenic agent, the daily individual ration of the dogs was divided into approximately equal small balls (15 to 20 g) which were offered to the dogs every 10 minutes for 8 hours. Normally the animals regularly accept the small balls successively when they are presented. The refusal shows anorexigenic efficacy of the test compound administered in gelules in the first small ball. The hourly number of refusal is determined in the animals treated with the same dose and is expressed as a percentage of the total hourly number of small balls presented per 6 animals. At the start of the test, the animals had been starved for about 15 hours although they had drinking water available. They are deprived of water during the test. The test was effected with a group of 7 bastard dogs both male and female weighing between 11.4 and 14 kg (12.1 kg average) selected as a function of their response to a weak dose (5 mg/kg) of fenfluramine. Under the test conditions, the compound of Example 1 showed an important oral anorexigenic activity at a dose of 10 mg/kg.

D. Acute toxicity

The DL$_{50}$ dose which kills 50% of mice after intraperitoneal administration of the test compound was determined 48 hours later and the DL$_{50}$ for the compounds is reported in Table III.

TABLE III

| Product of Example | DL$_{50}$ in mg/Kg |
|---|---|
| 1 | 100 |
| 2 | 200 |
| 3 | 150 |
| 4 | 100 |
| 5 | 200 |
| 6 | 400 |
| 7 | 150 |
| 8 | 150 |
| 17 | >400 |
| 18 | 100 |
| 19 | >200 |

Various modification of the products and methods of the invention may be made without departing from the spirit or scope thereof and it should be understood that the invention is intended to be limited only as defined in the appendix claims.

We claim:

1. A compound of the formula

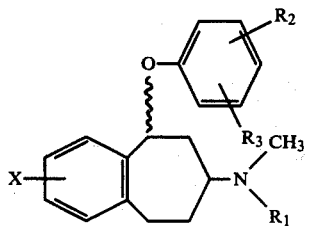

wherein R$_1$ is selected from the group consisting of hydrogen and methyl, R$_2$ and R$_3$ are individually selected from the group consisting of hydrogen, fluorine, chlorine, bromine, nitro, amino, —CF$_3$ and methoxy, X is selected from the group consisting of hydrogen and halogen and their non-toxic, pharmaceutically acceptable acid addition salts and the wavy line indicates that the substituent in the 5 position may be in the cis or trans form.

2. A compound of claim 1 wherein X is hydrogen.

3. A compound of claim 1 wherein R$_1$ is methyl.

4. A compound of claim 3 wherein at least one of R$_2$ and R$_3$ is hydrogen.

5. A compound of claim 1 selected from the group consisting of cis and trans N,N-dimethyl-5-[4-nitrophenoxy]-6,7,8,9-tetrahydro-5H-benzocyclohepten-7-amine and their non-toxic, pharmaceutically acceptable acid addition salts.

6. A compound of claim 1 selected from the group consisting of cis N,N-dimethyl-5-[4-trifluoromethylphenoxy]-6,7,8,9-tetrahydro-5H-benzocyclohepten-7-amine and their non-toxic, pharmaceutically acceptable acid addition salts.

7. A compound of claim 1 selected from the group consisting of cis N,N-dimethyl-5-[4-bromophenoxy]-6,7,8,9-tetrahydro-5H-benzocyclohepten-7-amine and their non-toxic, pharmaceutically acceptable acid addition salts.

8. A compound of claim 1 which is the fumarate of cis N,N-dimethyl-5-[4-nitrophenoxy]-6,7,8,9-tetrahydro-5H-benzocyclohepten-7-amine.

9. An anorexigenic composition comprising an anorexigenically effective amount of the compound of claim 8 and a pharmaceutical carrier.

10. A method of curbing the appetite of warm-blooded animals comprising administering to warm-blooded animals in need of such treatment an anorexigenically effective amount of the compound of claim 8.

11. A pharmaceutical antidepressive composition comprising an antidepressively effective amount of at least one compound of claim 1 and a pharmaceutical carrier.

12. A composition of claim 11 wherein X is hydrogen.

13. A composition of claim 11 wherein R$_1$ is methyl.

14. A composition of claim 11 wherein at least one of R$_2$ and R$_3$ is hydrogen.

15. A composition of claim 11 wherein the active ingredient is selected from the group consisting of cis and trans N,N-dimethyl-5-[4-nitrophenoxy]-6,7,8,9-tetrahydro-5H-benzocyclohepten-7-amine and their non-toxic, pharmaceutically acceptable acid addition salts.

16. A composition of claim 11 wherein the active ingredient is selected from the group consisting of cis N,N-dimethyl-5-[4-trifluoromethylphenoxy]-6,7,8,9-tetrahydro-5H-benzocyclohepten-7-amine and their non-toxic, pharmaceutically acceptable acid addition salts.

17. A composition of claim 11 wherein the active ingredient is selected from the group consisting of cis N,N-dimethyl-5-[4-bromophenoxy]-6,7,8,9-tetrahydro-5H-benzocyclohepten-7-amine and their non-toxic, pharmaceutically acceptable acid addition salts.

18. A composition of claim 11 wherein the active ingredient is the fumarate of cis N,N-dimethyl-5-[4-nitrophenoxy]-6,7,8,9-tetrahydro-5H-benzocyclohepten-7-amine.

19. A method of relieving depression in warm-blooded animals comprising administering to warm-blooded animals in need of such treatment an antidepressively effective amount of at least one compound of claim 1.

20. A method of claim 19 wherein X is hydrogen.

21. A method of claim 19 wherein R$_1$ is methyl.

22. A method of claim 19 wherein at least one of R$_2$ and R$_3$ is hydrogen.

23. The method of claim 19 wherein said compound is selected from the group consisting of cis and trans N,N-dimethyl-5-[4-nitrophenoxy]-6,7,8,9-tetrahydro-5H-benzocyclohepten-7-amine and their non-toxic, pharmaceutically acceptable acid addition salts.

24. The method of claim 19 wherein said compound is selected from the group consisting of cis N,N-dimethyl-5-[4-trifluoromethylphenoxy]-6,7,8,9-tetrahydro-5H-benzocyclohepten-7-amine and their non-toxic, pharmaceutically acceptable acid addition salts.

25. The method of claim 19 wherein said compound is selected from the group consisting of cis N,N-dimethyl-5-[4-bromophenoxy]-6,7,8,9-tetrahydro-5H-benzocyclohepten-7-amine and their non-toxic, pharmaceutically acceptable acid addition salts.

26. The method of claim 19 wherein said compound is the fumarate of cis N,N-dimethyl-5-[4-nitrophenoxy]-6,7,8,9-tetrahydro-5H-benzocyclohepten-7-amine.

* * * * *